United States Patent
Chen et al.

(10) Patent No.: US 7,652,146 B2
(45) Date of Patent: Jan. 26, 2010

(54) PROCESS FOR PREPARING 2-AMINOTHIAZOLE-5-CARBOXAMIDES USEFUL AS KINASE INHIBITORS

(75) Inventors: Bang-Chi Chen, Plainsboro, NJ (US); Rulin Zhao, Pennington, NJ (US); Bei Wang, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 723 days.

(21) Appl. No.: 11/049,815

(22) Filed: Feb. 3, 2005

(65) Prior Publication Data

US 2005/0176965 A1      Aug. 11, 2005

Related U.S. Application Data

(60) Provisional application No. 60/542,465, filed on Feb. 6, 2004.

(51) Int. Cl.
C07D 277/56      (2006.01)

(52) U.S. Cl. ..................................................... 548/194

(58) Field of Classification Search .................. 548/194
See application file for complete search history.

(56) References Cited

U.S. PATENT DOCUMENTS

| | | | | | |
|---|---|---|---|---|---|
| 2,441,498 | A | * | 5/1948 | Lofgren et al. | 564/194 |
| 3,796,800 | A | * | 3/1974 | Ariyan et al. | 514/370 |
| 6,277,995 | B1 | * | 8/2001 | Joe et al. | 548/149 |
| 6,344,562 | B1 | | 2/2002 | Alig et al. | |
| 6,596,746 | B1 | | 7/2003 | Das et al. | |
| 6,670,357 | B2 | | 12/2003 | Leftheris et al. | |
| 7,253,197 | B2 | * | 8/2007 | Guba et al. | 514/370 |
| 2004/0220233 | A1 | | 11/2004 | Hynes et al. | |
| 2006/0004067 | A1 | | 1/2006 | Chen et al. | |

FOREIGN PATENT DOCUMENTS

| | | | |
|---|---|---|---|
| GB | 2042528 A | * | 9/1980 |
| WO | WO 00/18766 | | 4/2000 |
| WO | WO 03/091229 | | 11/2003 |
| WO | WO 2005/077945 | | 8/2005 |

OTHER PUBLICATIONS

CA Registry No. 565171-06-4, Aug. 12, 2003.*
Autenrieth, W. et al., "Regarding our knowledge of the five isometric acids $C_4H_6O_2$", Chem. Ber., vol. 38, pp. 2534-2551 (1905) (with English translation).
Bredereck, H. et al., "Darstellung und Reaktionen substituierter Amidacetale", Chem. Ber., vol. 104, pp. 3475-3485 (1971).
Eremeev, A.V. et al., "Absolute Configuration of Diastereomeric Derivatives of N-Substituted Aziridine-2-Carboxylic Acids", Chem. Heterocycl. Compd. (Engl. Transl.), vol. 20, pp. 1102-1107 (1984).
Fèugeas, C. et al., "Préparation et propriétés de composés à structure trivalente mixte: dérivés diméthylamino-1 gemdialcoxy-1,1", J. Bull. Soc. Chim. Fr., No. 12, pp. 4985-4990 (1968).
Freear, J. et al., "Fluorinated Acetylenes. Part II. Certain Ionic and Radical Additions to NN-Bistrifluoromethylethynylamine", J. Chem. Soc. (C), pp. 411-416 (1969).
Friot, C. et al., "2,4-Diamino-1-Thia-3-Azabutadienes, Intermediates in Heterocyclic Synthesis", Phosphorus, Sulfur, and Silicon, vol. 156, pp. 135-149 (2000).
Greene, T.W. et al., Protective Groups in Organic Synthesis, Second Edition, John Wiley & Sons, Inc., publ., pp. ix-x (table of contents) (1991).
Hartmann, H. et al., "On the coupling of aryldiazonium salts with N,N-disubstituted 2-aminothiophenes and some of their carbocyclic and heterocyclic analogues", J. Chem. Soc., Perkin Trans. I, pp. 4316-4320 (2000).
Kantlehner, W., "Umsetzungen von Orthoamid-Derivaten mit Schwefel und Selen, Synthesen von 1,3-Thiazol- und 1,3-Selenazolderivaten", Journal für praktische Chemie Chemiker-Zeitung, vol. 338, pp. 403-413 (1996).
Kantlehner, W. et al., "Ein neues Herstellungsverfahren für 2,2,2-Trialkoxyacetonitrile und 2-Dialkylamino-2-alkoxycarbonsäurenitrile", Synthesis, pp. 358-360 (1984).
Knoll, A. et al., "Formylation Products of Thioamides; VII. Synthesis of New N-(3-Aminothioacryloyl)-formamidines and N,N'-Bis[aminomethylidene]thioureas by Bis-iminoformylation of Thioacetamides and Thiourea with Formamide Acetals", Synthesis, pp. 51-53 (1984).
Landreau, C. et al., "Cationic 1,3-Diazadienes in Annulation Reactions. Synthesis of Pyrimidine, Thiadiazinedioxide and Triazine Derivatives", J. Heterocyclic Chem., vol. 38, pp. 93-98 (2001).
Landreau, C. et al., "Cycloaddition Reactions Between 2,4-Diamino-1-Thia-3-Azabutadienes and Ketene. Synthesis of New 1,3-Thiazin-6-Ones, 1,3-Thiazine-6-Thiones and 2-Thioxopyrimidin-4-Ones", Heterocycles, vol. 53, No. 12, pp. 2667-2677 (2000).
Lin, Y.-i. et al., "New Synthesis of 1,2,4-Thiadiazoles", J. Org. Chem., vol. 45, No. 19, pp. 3750-3753 (1980).
Lin, Y.-i. et al., "The Synthesis of Substituted 2-Aminothiazoles", J. Heterocyclic Chem., vol. 16, pp. 1377-1383 (1979).
Marsham, P.R. et al., "Quinazoline Antifolate Thymidylate Synthase Inhibitors: Heterocyclic Benzoyl Ring Modifications", J. Med. Chem., vol. 34, pp. 1594-1605 (1991).
Noack, A. et al., "Herstellung und spektrale Charakterisierung neuartiger heteroanaloger Kristallviolett-Farbstoffe", Angew. Chem., vol. 113, No. 16, pp. 3097-3100 (2001).
Noack, A. et al., "Synthesis and characterisation of N,N-disubstituted 2-amino-5-acylthiophenes and 2-amino-5-acylthiazoles", Tetrahedron, vol. 58, pp. 2137-2146 (2002).

(Continued)

Primary Examiner—Laura L. Stockton
(74) Attorney, Agent, or Firm—Laurelee A. Duncan

(57) ABSTRACT

The invention is directed to processes for preparing 2-aminothiazole-5-carboxamides of formula I

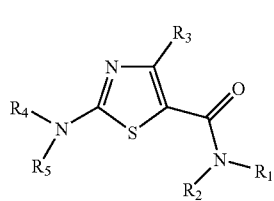

wherein $R_1$, $R_2$, $R_3$, $R_4$ and $R_5$ are as defined as set forth in the specification herein.

13 Claims, No Drawings

OTHER PUBLICATIONS

Oishi, T. et al., "The Reactions of Activated Amides. IV. The Reactions of Amide Acetals with Esters", Chem. Pharm. Bull., vol. 17, No. 11, pp. 2314-2318 (1969).

Raingeaud, J. et al., "MKK3- and MKK6-Regulated Gene Expression Is Mediated by the p38 Mitogen-Activated Protein Kinase Signal Transduction Pathway", Molecular and Cellular Biology, vol. 16, No. 3, pp. 1247-1255 (1996).

Roberts, E.C. et al., "Folic Acid Analogs. Modifications in the Benzene-Ring Region. 2. Thiazole Analogs", Journal of Medicinal Chemistry, vol. 15, No. 12, pp. 1310-1312 (1972).

Zhao, R. et al., "A new facile synthesis of 2-aminothiazole-5-carboxylates", Tetrahedron Letters, vol. 42, pp. 2101-2102 (2001).

Amin et al. Synthesis and Recations of 2-chloromethyl-3,1-benzoxazin-4-ones with Amines, Egyptian Journal of Chemistry, vol. 38(1), pp. 113-123, (1995).

Cutler, et al., "Synthesis of Cyclopenin and Cyclopenol Intermediates: Study of Analogue Structures and Biological Activities", Plant Growth Regulation Society of America, $27^{th}$, pp. 33-41, (2000).

Office Action of U.S. Appl. No. 11/271,626, filed Nov. 2008.

* cited by examiner

PROCESS FOR PREPARING 2-AMINOTHIAZOLE-5-CARBOXAMIDES USEFUL AS KINASE INHIBITORS

CROSS REFERENCE TO RELATED APPLICATION

This non-provisional application claims priority from provisional application U.S. Ser. No. 60/542,465, filed Feb. 6, 2004, the entirety of which is incorporated by reference herein.

FIELD OF THE INVENTION

The present invention concerns processes for the preparation of 2-aminothiazole-5-carboxamide compounds useful as kinase inhibitors.

BACKGROUND OF THE INVENTION

2-Aminothiazole-5-carboxamides of formula I

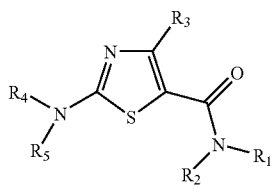

(I)

wherein,
$R_1$, $R_2$, $R_3$, $R_4$ and $R_5$ defined herein, are useful as kinase inhibitors, including inhibitors of p38 kinase. Inhibiting p38 enzymes in cells results in reduced levels of TNF-α expression, and administering p38 inhibitors in animal models of inflammatory disease has proven that these inhibitors are effective in treating inflammatory and immune conditions. 2-Aminothiazole-5-carboxamides of formula (I) herein, having activity as p38 inhibitors, are described in U.S. patent application Ser. No. 10/773,790, filed concomitantly with the provisional application from which the present application is based, claiming priority to U.S. Provisional application Ser. No. 60/445,410, filed Feb. 6, 2003 (hereinafter the '410 application), both of which are assigned to the present assignee and incorporated herein by reference.

Previous approaches for preparing 2-aminothiazole-5-carboxamides are described in U.S. Pat. No. 6,596,746 (the '746 patent), also assigned to the present assignee, and in the '410 application. The '746 patent describes a process involving treatment of chlorothiazole with n-BuLi followed by reaction with phenyl isocyanates to give chlorothiazolyl benzamides, which are further elaborated to aminothiazolyl benzamide final products after protection, chloro-to amino substitution, and deprotection, e.g.,

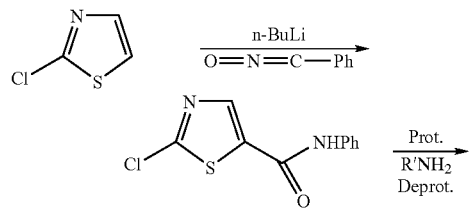

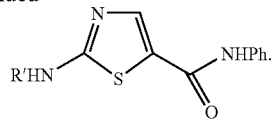

The '410 application describes a multi-step process involving first, converting N-unsubstituted aminothiazole carboxylic acid methyl or ethyl esters to bromothiazole carboxylic acid esters via diazotization with tert-butyl nitrite and subsequent $CuBr_2$ treatment, e.g.,

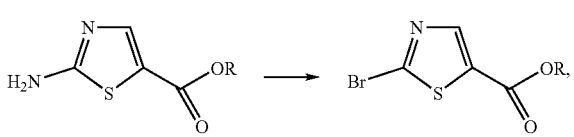

then, hydrolyzing the resulting bromothiazole esters to the corresponding carboxylic acids and converting the acids to the corresponding acyl chlorides, e.g.,

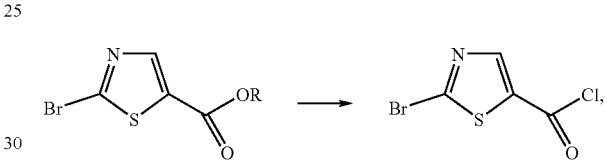

then finally, coupling the acyl chlorides with anilines to afford bromothiazole-benzamide intermediates which were further elaborated to aminothiazole-benzamide final products, e.g.,

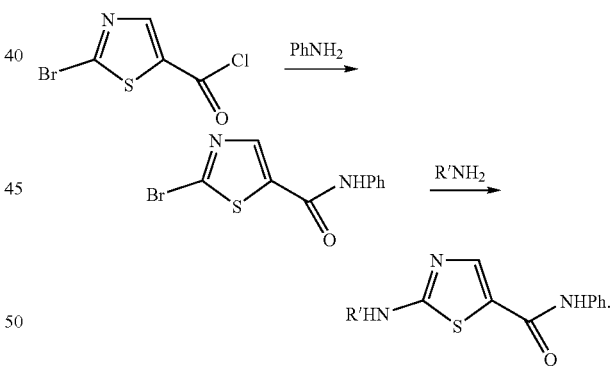

Other approaches for making 2-aminothiazole-5-carboxamides include coupling of 2-aminothiazole-5-carboxylic acids with amines using various coupling conditions such as DCC [Roberts et al, *J. Med. Chem.* (1972), 15, at p. 1310], and DPPA [Marsham et al., *J. Med. Chem.* (1991), 34, at p. 1594)].

The above methods present drawbacks with respect to the production of side products, the use of expensive coupling reagents, less than desirable yields, and the need for multiple reaction steps. New and efficient processes for preparing 2-aminothiazole-5-carboxamides are desired.

Reaction of N,N-dimethyl-N'-(aminothiocarbonyl)-formamidines with α-haloketones and esters to give 5-carbonyl-2-aminothiazoles has been reported. See Lin, Y. et al, *J. Heterocycl. Chem.* (1979), 16, at 1377; Hartmann, H. et al, *J.*

*Chem. Soc. Perkin Trans.* (2000), 1, at 4316; Noack, A. et al; *Tetrahedron* (2002), 58, at 2137; Noack, A.; et al. *Angew. Chem.* (2001), 113, at 3097; and Kantlehner, W. et al., *J. Prakt. Chem./Chem.-Ztg.* (1996), 338, at 403. Reaction of β-ethoxy acrylates and thioureas to prepare 2-aminothiazole-5-carboxylates also has been reported. Zhao, R., et al., *Tetrahedron Lett.* (2001), 42, at 2101. However, electrophilic bromomination of acrylanilide and crotonanilide has been known to undergo both aromatic bromination and addition to the α,β-unsaturated carbon-carbon double bonds. See Autenrieth, *Chem. Ber.* (1905), 38, at 2550; Eremeev et al., *Chem. Heterocycl. Compd. Engl. Transl.* (1984), 20, at 1102.

SUMMARY OF THE INVENTION

Summarily described, the invention is related to a process for preparing 2-aminothiazole-5-carboxamides having the formula (I),

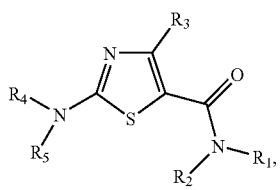

(I)

wherein $R_1$, $R_2$, $R_3$, $R_4$ and $R_5$ are as defined below, comprising, (i) reacting a compound having the formula (II),

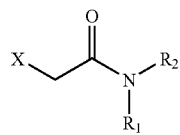

(II)

wherein X is a leaving group, and $R_1$ and $R_2$ are as defined below, (ii) with a compound having the formula (III)

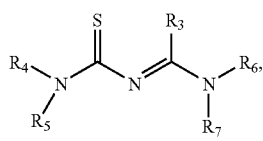

(III)

wherein $R_3$, $R_4$ and $R_5$ are as defined below and $R_6$ and $R_7$ are (i) independently selected from alkyl, substituted alkyl, alkenyl, substituted alkenyl, alkynyl, substituted alkynyl, aryl, heteroaryl, cycloalkyl, and heterocyclo, or alternatively, (ii) $R_6$ and $R_7$ are taken together to form heteroaryl or heterocyclo;

(iii) to provide the compound having formula (I), above, wherein, $R_1$ (i) is the same in each of formulae (I) and (II), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_1$ is taken together with $R_2$, to form heteroaryl or heterocyclo;

$R_2$ (i) is the same in each of formulae (I) and (II), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_2$ is taken together with $R_1$, to form heteroaryl or heterocyclo;

$R_3$ is the same in each of formulae (I) and (III), and is selected from hydrogen, cyano, haloalkyl, alkyl, substituted alkyl, alkenyl, substituted alkenyl, aryl, heteroaryl, cycloalkyl, and heterocyclo;

$R_4$ (i) is the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_4$ is taken together with $R_5$, to form heteroaryl or heterocyclo; and $R_5$ (i) is the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_5$ is taken together with $R_4$, to form heteroaryl or heterocyclo.

DETAILED DESCRIPTION OF THE INVENTION

Abbreviations

For ease of reference, the following abbreviations may be used herein:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMF-DMA=N,N-dimethylformamide dimethyl acetal
DMSO=dimethyl sulfoxide
DPPA=diphenylphosphoryl azide
DPPF=1,1'-bis(diphenylphosphino)ferrocene
HATU=O-benzotriazol-1-yl0 N,N,N',N'-tetramethyluronium hexafluorphosphate
LDA=lithium di-isopropyl amide
TEA=triethylamine
TFA=trifluoroacetic acid
THF=tetrahydrofuran
KOH=potassium hydroxide
$K_2CO_3$=potassium carbonate
$POCl_3$=phosphorous oxychloride
EDC or EDCI=3-ethyl-3'-(dimethylamino)propyl-carbodiimide
DIPEA=diisopropylethylamine
HOBt=1-hydroxybenzotriazole hydrate
NBS=N-bromosuccinamide
NMP=N-methyl-2-pyrrolidinone
NaH=sodium hydride
NaOH=sodium hydroxide
$Na_2S_2O_3$=sodium thiosulfate
Pd=palladium
Pd—C or Pd/C=palladium on carbon min=minute(s)
L=liter
mL=milliliter
μL=microliter
g=gram(s)
mg=milligram(s)
mol=moles
mmol=millimole(s)
meq=milliequivalent
RT or rt=room temperature
RBF=round bottom flask
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point Definitions The following are definitions of terms used in this specification and appended claims. The initial definition provided for a group or term herein applies to that group or term throughout the specification and claims, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are most preferred.

The term "substituted alkyl" refers to an alkyl group substituted with one or more substituents (preferably 1 to 4 substituents, even more preferably 1 to 2 substituents) at any available point of attachment. Exemplary substituents may be selected from one or more (preferably 1 to 3) of the following groups:

(i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —$S(=O)R_e$, —$S(=O)_2R_e$, —$S(=O)_3H$, —$P(=O)_2$—$R_e$, —$S(=O)_2OR_e$, —$P(=O)_2OR_e$, —$U_1$—$NR_bR_c$, —$U_1$—$N(R_d)$—$U_2$—$NR_bR_c$, —$U_1$—$NR_d$—$U_2$—$R_b$, —$NR_bP(=O)_2R_e$, —$P(=O)_2NR_bR_c$, —$C(=O)OR_e$, —$C(=O)R_a$, —$OC(=O)R_a$, —$NR_dP(=O)_2NR_bR_c$, —$R_bP(=O)_2R_e$, —$U_1$-aryl, —$U_1$-heteroaryl, —$U_1$-cycloalkyl, —$U_1$-heterocyclo, —$U_1$-arylene-$R_e$, —$U_1$-heteroarylene-$R_e$, —$U_1$-cycloalkylene-$R_e$, and/or —$U_1$-heterocyclene-$R_e$, wherein, in group (i), (ii) —$U_1$— and —$U_2$— are each independently a single bond, —$U^3$—$S(O)_t$—$U^4$—, —$U^3$—$C(O)$—$U^4$—, —$U^3$—$C(S)$—$U^4$—, —$U^3$—$O$—$U^4$—, —$U^3$—$S$—$U^4$—, —$U^3$—$O$—$C(O)$—$U^4$—, —$U^3$—$C(O)$—$O$—$U^4$—, or —$U^3$—$C(=NR_g)$—$U^4$—;

wherein, (iii) $U^3$ and $U^4$ are each independently a single bond, alkylene, alkenylene, or alkynylene;

wherein, in group (i), (iv) $R_a$, $R_b$, $R_c$, $R_d$, and $R_e$ are each independently hydrogen, alkyl, alkenyl, alkynyl, cycloalkyl, aryl, heterocyclo, or heteroaryl, each of which is unsubstituted or substituted with one to four groups $R_f$, except $R_e$ is not hydrogen; or $R_b$ and $R_c$ may be taken together to form a 3- to 8-membered saturated or unsaturated ring together with the atoms to which they are attached, which ring is unsubstituted or substituted with one to four groups listed below for $R_f$; or $R_b$ and $R_c$ together with the nitrogen atom to which they are attached may combine to form a group —N=C $R_gR_h$ where $R_g$ and $R_h$ are each independently hydrogen, alkyl, or alkyl substituted with a group $R_f$; and;

wherein, (v) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vi) t is 0, 1 or 2.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. A substituted alkenyl refers to an alkenyl having one or more substituents (preferably 1 to 3 substituents, even more preferably 1 to 2 substituents), selected from those defined above for substituted alkyl.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. A substituted alkynyl refers to an alkynyl having one or more substituents (preferably 1 to 4 substituents, even more preferably 1 to 2 substituents), selected from those defined above for substituted alkyl.

When the term "alkyl" is used as a suffix with another group, such as in (aryl)alkyl or arylalkyl, this conjunction is meant to refer to a substituted alkyl group wherein at least one of the substituents is the specifically named group in the conjunction. For example, (aryl)alkyl refers to a substituted alkyl group as defined above wherein at least one of the alkyl substituents is an aryl, such as benzyl. However, in groups designated —O(alkyl) and —S(alkyl), it should be understood that the points of attachment in these instance are to the oxygen and sulfur atoms, respectively.

Where alkyl groups as defined are divalent, i.e., with two single bonds for attachment to two other groups, they are termed "alkylene" groups. Similarly, where alkenyl groups as defined above and alkynyl groups as defined above, respectively, are divalent radicals having single bonds for attachment to two other groups, they are termed "alkenylene groups" and "alkynylene groups" respectively. Examples of alkylene, alkenylene and alkynylene groups include:

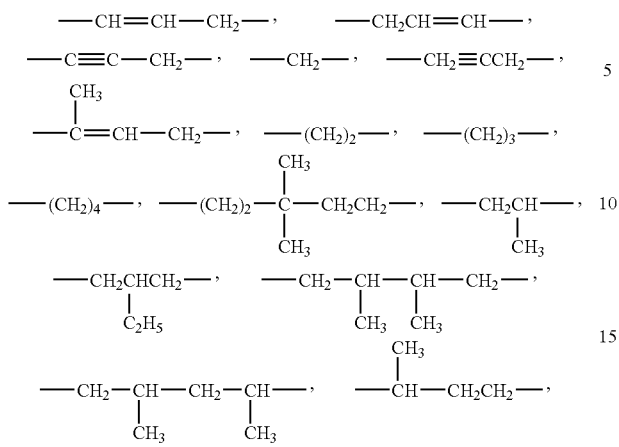

and the like. Alkylene groups may be optionally independently substituted as valence allows with one or more groups as defined for substituted alkyl groups. Thus, for example, a substituted alkylene group would include

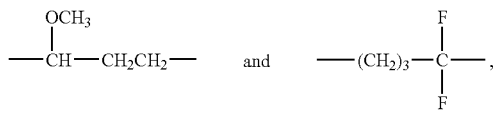

and so forth.

The term "cycloalkyl" as used herein by itself or as part of another group refers to optionally-substituted saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The further rings of multi-ring cycloalkyls may be either fused, bridged and/or joined through one or more spiro union. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cycloheptenyl, cyclooctenyl, cyclohexadienyl, cycloheptadienyl,

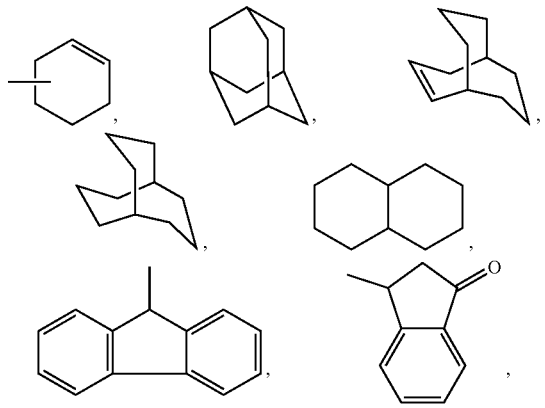

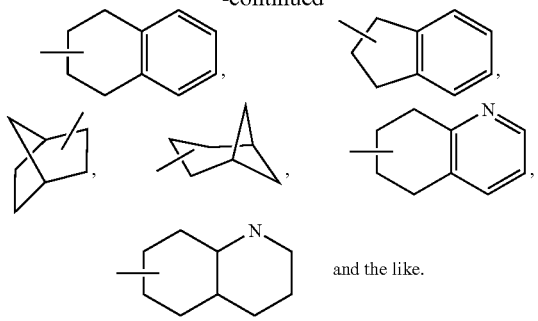

and the like.

Each reference to a cycloalkyl is intended to include both substituted and unsubstituted cycloalkyl groups as defined immediately below, unless reference is made to a particular selection of substituents to be made for the cycloalkyl (e.g., wherein cycloalkyl is substituted with one or more groups $R_f$). When no particular selection is recited, the optional substituents for the cycloalkyl groups may be selected from the following:

(i) halogen (e.g., a single halo substituent or multiple halo substitutents forming, in the latter case, groups such as a perfluoroalkyl group or an alkyl group bearing $Cl_3$ or $CF_3$), haloalkoxy, cyano, nitro, oxo (=O), —$OR_a$, —$SR_a$, —S(=O)$R_e$, —S(=O)$_2R_e$, —S(=O)$_3$H, —P(=O)$_2$—$R_e$, —S(=O)$_2OR_e$, —P(=O)$_2$OR, —$U_1$—$NR_bR_c$, —$U_1$—N($R_d$)—$U_2$—$NR_bR_c$, —$U_1$—$NR_d$—$U_2$—$R_b$, —$NR_bP$(=O)$_2R_e$, —P(=O)$_2NR_bR_c$, —C(=O)OR, —C(=O)$R_a$, —OC(=O)$R_a$, —$NR_d$P(=O)$_2NR_bR_c$, —$R_b$P(=O)$_2R_e$, and/or —U—$R_e$, and/or (ii) —$U_1$-alkyl, —$U_1$-alkenyl, or —$U_1$-alkynyl wherein the alkyl, alkenyl, and alkynyl are substituted with one or more (preferably 1 to 3) groups recited in (i), wherein, in groups (i) and (ii), (iii) —$U_1$— and —$U_2$— are each independently a single bond, —$U^3$—S(O)$_t$—$U^4$—, —$U^3$—C(O)—$U^4$—, —$U^3$—C(S)—$U^4$—, —$U^3$—O—$U^4$—, —$U^3$—S—$U^4$—, —$U^3$—O—C(O)—$U^4$—, —$U^3$—C(O)—O—$U^4$—, or —$U^3$—C(=$NR_g$)—$U^4$—;

wherein, in group (iii), (iv) $U^3$ and $U^4$ are each independently a single bond, alkylene, alkenylene, or alkynylene;

wherein, (v) $R_a$, $R_b$, $R_c$ $R_d$, and $R_e$ are each independently hydrogen, alkyl, alkenyl, alkynyl, cycloalkyl, aryl, heterocyclo, or heteroaryl, each of which is unsubstituted or substituted with one or more groups $R_f$, except $R_e$ is not hydrogen; or $R_b$ and $R_c$ may be taken together to form a 3- to 8-membered saturated or unsaturated ring together with the atoms to which they are attached, which ring is unsubstituted or substituted with one or more groups listed below for $R_f$, or $R_b$ and $R_c$ together with the nitrogen atom to which they are attached may combine to form a group —N=C $R_gR_h$, where $R_g$ and $R_h$ are each independently hydrogen, alkyl, or alkyl substituted with a group $R_f$; and;

wherein, (vi) $R_f$ is at each occurrence independently selected from alkyl, halogen, cyano, hydroxy, —O(alkyl), SH, —S(alkyl), amino, alkylamino, haloalkyl, haloalkoxy, or a lower alkyl substituted with one to two of halogen, cyano, hydroxy, —O(alkyl), SH, —S(alkyl), amino, alkylamino, haloalkyl, and/or haloalkoxy, and wherein, (vii) t is 0, 1 or 2.

When the suffix "ene" is used in conjunction with a cyclic group, this is intended to mean the cyclic group as defined herein having two single bonds as points of attachment to other groups. Thus, for example, the term "cycloalkylene" as employed herein refers to a "cycloalkyl" group as defined above which is a linking group such as

 and the like.

The term "alkoxy" refers to an alkyl or substituted alkyl group as defined above bonded through an oxygen atom (—O—), i.e., the group —OR$_i$, wherein R$_i$ is alkyl or substituted alkyl.

The term "alkylthio" refers to an alkyl or substituted alkyl group as defined above bonded through a sulfur atom (—S—), i.e., the group —SR$_i$, wherein R$_i$ is alkyl or substituted alkyl.

The term "acyl" refers to a carbonyl group linked to an alkyl radical, more particularly, the group C(=O)R$_j$, wherein R$_j$ can be selected from alkyl, alkenyl, substituted alkyl, or substituted alkenyl, as defined herein.

The term "alkoxycarbonyl" refers to a carboxy group

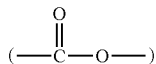

linked to an alkyl radical (CO$_2$R$_j$), wherein R$_j$ is as defined above for acyl. When the designation "CO$_2$" is used herein, this is intended to refer to the group

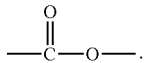

The term "alkylamino" refers to amino groups wherein one or both of the hydrogen atoms is replaced with an alkyl group, i.e., NR$_k$R$_l$, wherein one of R$_k$ and R$_l$ is hydrogen and the other is alkyl, or both R$_k$ and R$_l$ are alkyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The terms "ar" or "aryl" as used herein by itself or as part of another group refer to optionally-substituted aromatic homocyclic (i.e., hydrocarbon) monocyclic, bicyclic or tricyclic aromatic groups containing 6 to 14 carbons in the ring portion [such as phenyl, biphenyl, naphthyl (including 1-naphthyl and 2-naphthyl) and antracenyl], and may optionally include one to three additional rings (either cycloalkyl, heterocyclo or heteroaryl) fused thereto. Examples include:

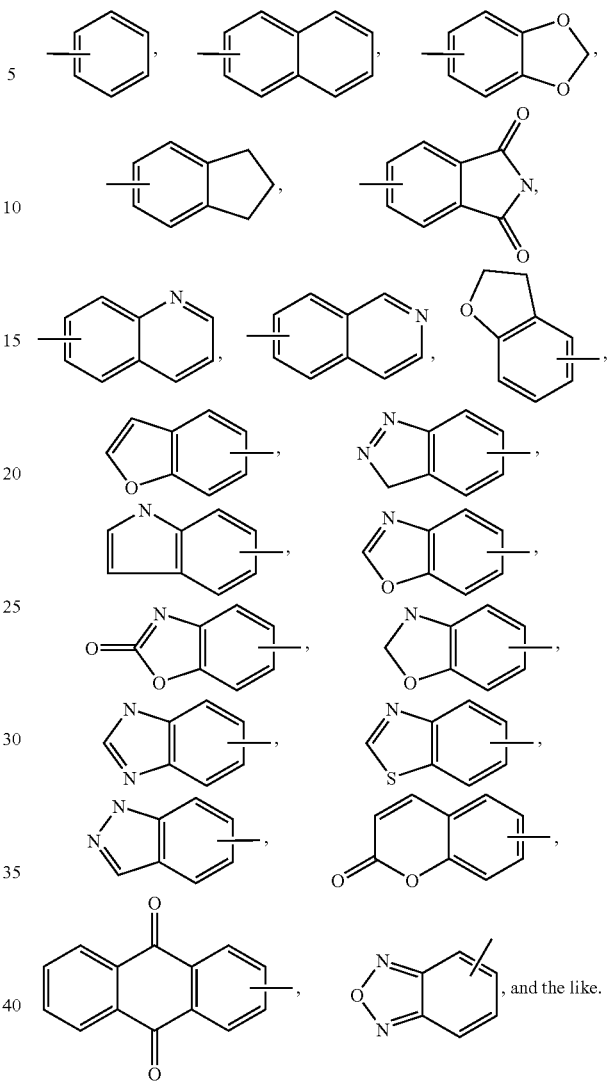 and the like.

Each reference to an aryl is intended to include both substituted and unsubstituted aryl groups as defined herein, unless reference is made to a particular selection of substituents to be made for the aryl (e.g., as when aryl is substituted with one or more groups R$_f$, above). When no particular selection is recited, the optional substituents for the aryl groups may be selected from those recited above, as valence allows, for cycloalkyl groups.

The term "heteroaryl" as used herein by itself or as part of another group refers to optionally-substituted monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

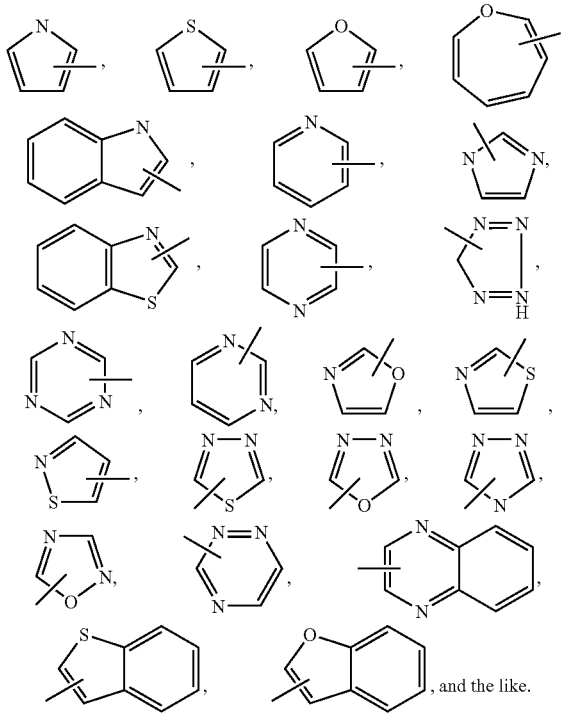

, and the like.

Each reference to a heteroaryl is intended to include both substituted and unsubstituted heteroaryl groups as defined herein, unless reference is made to a particular selection of substituents to be made for the heteroaryl (e.g., as when heteroaryl is substituted with one or more groups $R_f$, above). When no particular selection is recited, the optional substituents for the heteroaryl groups may be selected from those recited above, as valence allows, for cycloalkyl groups.

The terms "heterocyclic" or "heterocyclo" as used herein by itself or as part of another group refer to non-aromatic, optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be fused, bridged and/or joined through one or more spiro unions.

Exemplary heterocyclic groups include oxetanyl, imidazolinyl, oxazolidinyl, isoxazolinyl, thiazolidinyl, isothiazolidinyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

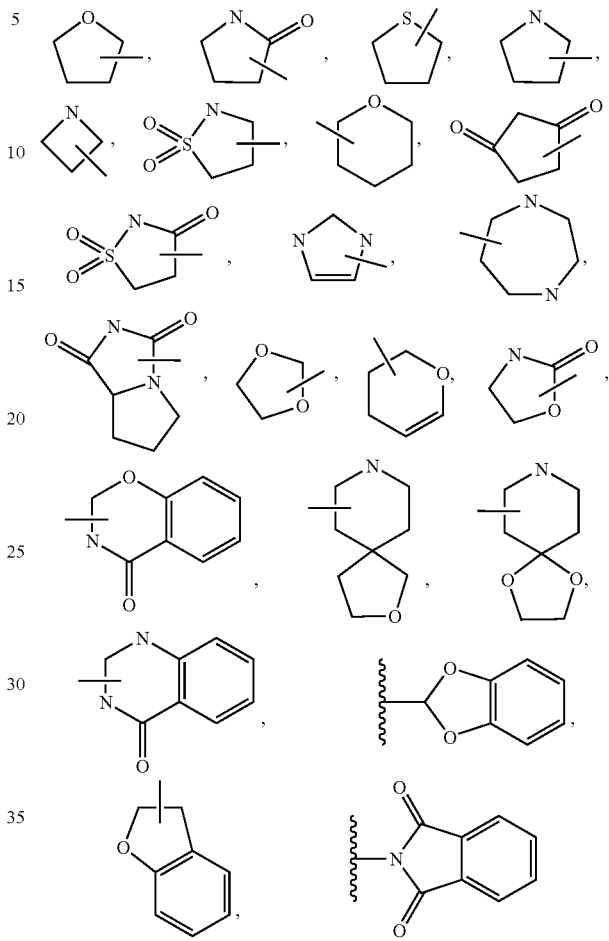

and the like, which optionally may be substituted.

Each reference to a heterocyclo is intended to include both substituted and unsubstituted heterocyclo groups as defined herein, unless reference is made to a particular selection of substituents to be made for the heterocyclo (e.g., as when heterocyclo is substituted with one or more groups $R_f$, above). When no particular selection is recited, the optional substituents for the heterocyclo groups may be selected from those recited above, as valence allows, for cycloalkyl groups.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated, the reference is intended to include rings having 0 to 3, preferably 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

"Base" when used herein includes metal oxides, hydroxides or alkoxides, hydrides, or compounds such as ammonia, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, more preferably where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide ($Mg(OH)_2$) or calcium hydroxide ($Ca(OH)_2$); alkali metal hydrides (i.e., MH, wherein M is as defined above, thus including, without limitation, sodium hydride and lithium hydride); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$), alkyl ammonium hydroxides such as n-tetrabutyl ammonium hydroxide (TBAH); and so forth. Preferred bases herein include organic bases more particularly tertiary amines such as N-methylmorpholine, triethylamine, and diisopropylethylamine.

The term "coupling reagent" as used herein refers to a reagent used to couple a carboxylic acid and an amine or an aniline to form an amide bond. It may include a coupling additive, such as CDI, HOBt, HOAt, HODhbt, HOSu, or NEPIS, used in combination with another coupling reagent to speed up coupling process and inhibit side reactions. Particular peptide-coupling reagents may include DCC, EDC, BBC, BDMP, BOMI, HATU, HAPyU, HBTU, TAPipU, AOP, BDP, BOP, PyAOP, PyBOP, TDBTU, TNTU, TPTU, TSTU, BEMT, BOP—Cl, BroP, BTFFH, CIP, EDPBT, Dpp-Cl, EEDQ, FDPP, HOTT-PF6, TOTT-BF4, PyBrop, PyClop, and TFFH. See "Peptide Coupling Reagents: Names, Acronyms and References," Albany Molecular Research, Inc., Technical Reports, Vol. 4, No. 1, incorporated herein by reference.

"High yield" as used herein means a yield of greater than 80%, more preferably greater than 85%, even more preferably greater than 90%, and most preferably greater than 95%.

"Leaving group" means groups having the capability of being displaced upon reaction with a nucleophile including I, Br, Cl, $R_m SO_2 O$— (wherein $R_m$ is alkyl, substituted alkyl, aryl, or heteroaryl, as defined herein), weak bases, such as, for example, $HSO_4$—. Preferred leaving groups include I, Br, Cl, and ions of methyl sulfate, mesylate (methane sulfonate), trifluoromethanesulfonate, and tosylate (p-toluenesulfonate).

"Protecting group" refers to those groups that one skilled in the field would readily recognize as being suitable to protect an amine or other group and which may be removed under typical deprotection conditions well known to those skilled in the field, e.g., which can be selected from Greene and Wuts, *Protecting Groups in Organic Synthesis* (John Wiley & Sons, New York 1991), incorporated herein by reference.

"Suitable solvent" as used herein is intended to refer to a single solvent as well as mixtures of solvents. Solvents may be selected, as appropriate for a given reaction step, from, for example, aprotic polar solvents such as DMF, DMA, DMSO, dimethylpropyleneurea, N-methylpyrrolidone, and hexamethylphosphoric triamide; ether solvents such as diethyl ether, THF, 1,4-dioxane, methyl t-butyl ether, dimethoxymethane, and ethylene glycol dimethyl ether; alcohol solvents such as MeOH, EtOH, and isopropanol; and halogen-containing solvents such as methylene chloride, chloroform, carbon tetrachloride, and 1,2-dichloroethane.

General Method

The invention is related to processes for the preparation of 2-aminothiazole-5-carboxamides which are useful as kinase inhibitors, more particularly inhibitors of p38 kinase and Src kinase. The process involves [1+4]-cycloaddition of acetamides having the formula (II),

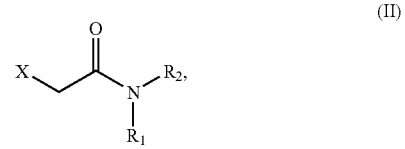

wherein $R_1$ and $R_2$ are as defined in the Summary of Invention and X is a leaving group as described above, such as Cl, Br, I (e.g., α-haloacetamides, or α-sulfonyloxyacetamides), with N,N-disubstituted-N'-(aminothiocarbonyl)-amidines of formula (III),

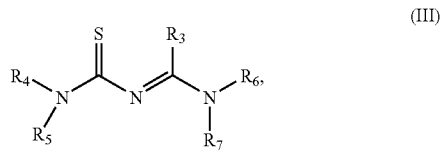

wherein $R_3$, $R_4$, $R_5$, $R_6$ and $R_7$ are as defined in the Summary of Invention, to give 2-aminothiazole-5-carboxamides of formula (I). The reaction is carried out in a suitable solvent optionally in the presence of base, but preferably, no base is used. Suitable solvent(s) include solvents such hydrocarbons, halogenated hydrocarbons, ethers, esters, amides, ketones and alcohols with alcohols such as methanol preferred. The reaction may be carried out at room temperature, or heat may be applied. As one skilled in the field may appreciate, this reaction provides an efficient method of producing compounds of formula (I) in high yield.

Preferably, in compounds of formula (II), X is Cl, Br, or I, more preferably Cl. Preferably one of $R_1$ and $R_2$ is hydrogen and the other is a radical other than hydrogen, e.g., alkyl, aryl, or heteroaryl, more preferably, $R_1$ is hydrogen and $R_2$ is substituted aryl, more preferably phenyl, and even more preferably phenyl substituted with one to three of alkyl, halogen, —C(=O)$NR_8$, and/or $NR_8$C(=O), wherein $R_8$ is alkyl, cycloalkyl, or heteroaryl. N,N-Disubstituted α-haloacetamides and N-monosubstituted acetamides advantageously may be used, with the latter preferred. Preferably, in compounds of formula (III), $R_3$ is hydrogen. Also preferred are compounds of formula (III), wherein $R_6$ and $R_7$ are both lower alkyl, more preferably methyl. Also preferred are compounds wherein one of $R_4$ and $R_5$ is hydrogen and the other is a radical other than hydrogen, even more preferably wherein $R_4$ is hydrogen and $R_5$ is alkyl or aryl, more preferably lower alkyl such as 1-methyl-propyl.

Preparation of Intermediates of Formula (II)

The intermediate acetamides can be prepared by coupling compounds of formula (2a) wherein X is as defined herein wherein T is Cl, Br, I, or OH, with amines having desired substituents (2b), e.g.,

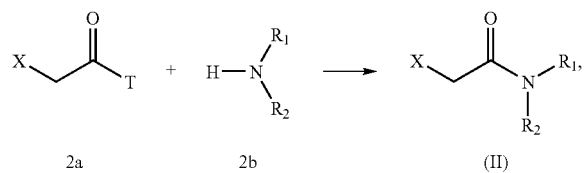

wherein, when T is OH, the reaction is carried out in the presence of a coupling reagent. Advantageously this reaction is carried out in the presence of base in a suitable solvent or solvent mixture. Suitable bases include inorganic and organic bases with organic bases preferred. The most preferred bases are tertiary amines such as N-methylmorpholine, triethylamine, and diisopropylethylamine. Suitable solvent(s) include solvents such hydrocarbons, ethers, esters, amides and ketones with ketones such as acetone preferred.

Preferably, compounds (2a) are α-haloacetyl halides or α-sulfonyloxyacetyl halides. The α-haloacetyl halides may include α-chloro, α-bromo, α-iodoacetyl chlorides, and α-chloro, α-bromo, α-iodoacetyl bromides. The preferred α-haloacetyl halides are α-chloroacetyl chloride, α-bromoacetyl chloride and α-bromoacetyl bromide with α-chloroacetyl chloride preferred. In compounds (2b), preferably one of $R_1$ and $R_2$ are as defined above.

Preparation of Intermediates of Formula (III)

The aminothiocarbonyl-amidine intermediates (III) can be prepared by reaction of thioureas (3a) with dialkoxy-N,N-disubstituted-alkylamines (3b),

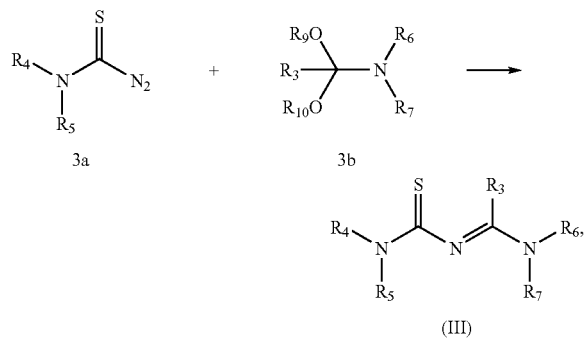

wherein $R_3$, $R_4$, $R_5$, $R_6$, and $R_7$ are as defined in the Summary of Invention, and $R_9$ and $R_{10}$ are alky, more preferably lower alkyl, more preferably methyl. The thioureas may include N,N-disubstituted thioureas and N-monosubstituted thioureas with the latter preferred. The 1,1-dimethoxy-N,N-dimethylalkylamines may include 1,1-dimethoxy-N,N-dimethylethanamine and 1,1-dimethoxy-N,N-dimethylmethanamine with the latter preferred. Suitable solvent(s) include solvents such as hydrocarbons, ethers, esters, amides, ketones and alcohols with alcohols such as ethanol preferred.

Compounds (3b) wherein $R_3$ is hydrogen, $R_6$, and $R_7$ are both methyl, and $R_9$ and $R_{10}$ are both methyl, are commercially available and thus preferred. However, one skilled in the field may make various modifications to these groups, for example, following procedures known in the literature. Preparation of N,N-dimethyl-N'-(aminothiocarbonyl)-formamidines has been previously reported [Lin, Y. et al., *J. Heterocycl. Chem.* (1979), 16, at 1377; Lin, Y. et al., *J. Org. Chem.* (1980), 45, at 3750; Friot, C. et al.; *Phosphorus, Sulfur Silicon Ralat. Elem.* (2000), 156, at 135; Landreau, C. et al, *Heterocycles* (2000), 53, at 2667; Landreau, C. et al., *J. Heterocyl. Chem.* (2001), 38, at 93; and Knoll, A. et al; *Synthesis* (1984), at 51]. Additionally, N,N-dimethyl-N'-(aminothiocarbonyl)-formamidines can be prepared according to Feugea C., et al.,*J. Bull. Soc. Chim Fr.* (1968), at 4985; Bredereck et al., *Chem. Ber.*, (1971), 104 at 3475; Freear et al., *J. Chem. Soc. C.* (1969), at 411; Oishi et al., *Chem Pharm. Bull.*, (1969), 17 at 2314; and Kantlehner et al., *Synthesis* (1984) at 358.

In one embodiment, the invention deals with the preparation of N-aryl 2-aminothiazole-5-carboxamides of formula (I), wherein $R_1$ =$R_3$=$R_4$=H, and $R_2$=aryl, more preferably substituted phenyl, useful as inhibitors of p38 kinase. In one embodiment, the process involves [1+4]-cycloaddition of α-haloacetamides, wherein X=Cl, Br, $R_1$=H, and $R_2$=aryl, with N,N-dimethyl-N'-(aminothiocarbonyl)-formamidines, wherein $R_3$=$R_4$=H, to give N-aryl 2-aminothiazole-5-carboxamides of formula (I).

Utility

The compounds of formula (I), made according to the inventive process herein, are useful as inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the compounds of formula (I) may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The compounds of formula (I) also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies, and other conditions.

The compounds of formula (I) also may be used to treat angiogenic disorders including solid tumors, ocular neovasculization, and infantile haemangiomas.

When the terms "p38 associated condition" or "p38 associated disease or disorder" are used herein, each is intended to encompass all of the conditions identified above as if repeated at length, as well as any other condition that is modulated by p38 kinase activity, for example, such as those recited in U.S. Pat. No. 6,670,357 B2, incorporated herein by reference.

The present invention also provides methods of preparing pharmaceutical compositions capable of treating p38-kinase associated conditions, including TNF-α, IL-1, and/or IL-8 mediated conditions, wherein the methods comprise making compounds of Formula (I) according to the inventive process herein and further preparing therefrom the pharmaceutical compositions, e.g., with one or more diluents or vehicles for administration. The said compositions may contain other therapeutic agents as known in the field. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The said pharmaceutical compositions may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds of formula (I) may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds of formula (I), prepared according to the inventive process, may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of formula (I) may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient"

is used herein, this term is intended to include all subjects, most preferably mammalian species, that are affected by mediation of p38 enzyme levels.

Compounds within the scope of formula (I) may be tested for activity as inhibitors of p38α/β enzymes and TNF-α using the assays described below, or variations thereof that are within the level ordinary skill in the art.

Compounds described in Examples 6-101 herein have been tested and shown activity as kinase inhibitors, in particular, inhibitors of Src kinase, p38α/β enzymes, and/or TNF-α.

Biological Assays

Generation of p38 Kinases cDNAs of human p38α, β and γ isozymes are cloned by PCR. These cDNAs can be subcloned in the pGEX expression vector (Pharmacia). GST-p38 fusion protein is expressed in *E. Coli* and purified from bacterial pellets by affinity chromatography using glutathione agarose. p38 fusion protein is activated by incubating with constitutively active MKK6. Active p38 is separated from MKK6 by affinity chromatography. Constitutively active MKK6 is generated according to Raingeaud et al. [*Mol. Cell. Biol.*, 1247-1255 (1996)].

TNF-α Production by LPS-Stimulated PBMCs

Heparinized human whole blood is obtained from healthy volunteers. Peripheral blood mononuclear cells (PBMCs) are purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension is incubated with 50 ul of test compound (4× concentration in assay medium containing 0.2% DMSO) in 96-well tissue culture plates for 5 minutes at RT. 100 ul of LPS (200 ng/ml stock) is then added to the cell suspension and the plate is incubated for 6 hours at 37° C. Following incubation, the culture medium is collected and stored at −20° C. TNF-α concentration in the medium is quantified using a standard ELISA kit (Pharmingen-San Diego, Calif.). Concentrations of TNF-α and $IC_{50}$ values for test compounds (concentration of compound that inhibited LPS-stimulated TNF-α production by 50%) are calculated by linear regression analysis.

p38 Assay

The assays are performed in V-bottomed 96-well plates. The final assay volume is 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 is pre-incubated with test compounds for 10 min. prior to initiation of reaction with substrates. The reaction is incubated at 25° C. for 45 min. and terminated by adding 5 μl of 0.5 M EDTA to each sample. The reaction mixture is aspirated onto a pre-wet filtermat using a Skatron Micro96 Cell Harvester (Skatron, Inc.), then washed with PBS. The filtermat is then dried in a microwave oven for 1 min., treated with MeltilLex A scintillation wax (Wallac), and counted on a Microbeta scintillation counter Model 1450 (Wallac). Inhibition data are analyzed by nonlinear least-squares regression using Prizm (GraphPadSoftware). The final concentration of reagents in the assays are ATP, 1 μM; [γ-$^{33}$P]ATP, 3 nM; MBP (Sigma, #M1891), 2 μg/well; p38, 10 nM; and DMSO, 0.3%.

TNF-α Production by LPS-Stimulated Mice

Mice (Balb/c female, 6-8 weeks of age, Harlan Labs; n=8/treatment group) are injected intraperitoneally with 50 ug/kg lipopolysaccharide (LPS; *E coli* strain 0111:B4, Sigma) suspended in sterile saline. Ninety minutes later, mice are sedated by $CO_2$:$O_2$ inhalation and a blood sample was obtained. Serum is separated and analyzed for TNF-alpha concentrations by commercial ELISA assay per the manufacturer's instructions (R&D Systems, Minneapolis, Minn.).

Test compounds are administered orally at various times before LPS injection.

The compounds are dosed either as suspensions or as solutions in various vehicles or solubilizing agents.

The following examples illustrate the invention but should not be interpreted as a limitation thereon.

EXAMPLES

Compounds of Formula (II)

Examples 1 through 3 illustrate specific examples for making compounds of Formula (II).

Example 1

3-(2-Chloroacetamido)-N-cyclopropyl-4-methylbenzamide

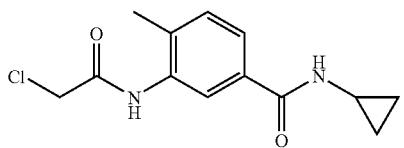

Step 1A

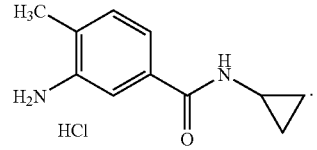

(1A)

A solution of 4-methyl-3-nitrobenzoyl chloride (69 g, 0.36 mol) in $CH_2Cl_2$ (400 mL) was cooled to 0° C., and then TEA (53 mL, 0.38 mol) was slowly added. A solution of cyclopropyl amine (25 g, 0.44 mol) in $CH_2Cl_2$ was added over 45 minutes while the internal reaction temperature was maintained below 5° C. The reaction was stirred for 1 h and then transferred to a separatory funnel with an additional 300 mL of $CH_2Cl_2$. This was then washed with 5% aq. HCl (500 mL) and brine (250 mL). The organic layer was dried over $Na_2SO_4$, filtered and concentrated. The crude solids were dissolved in hot EtOH (ca. 10 mL/g crude). Decolorizing carbon was added, and the reaction mixture was filtered through celite and concentrated again to produce a crude solid product. $^1$H NMR: ($CDCl_3$, 400 MHz) δ 8.23 (d, J=1.7 Hz, 1H), 7.87 (dd, J=1.7, 7.9 Hz, 1H), 7.24 (d, J=8 Hz, 1H), 6.44 (br s, 1H), 2.85 (m, 1H), 2.57 (s, 3H), 0.82 (m, 2H), 0.59 (m, 2H); LCMS 221.1 (M+H); HPLC rt 2.71 min.

To a suspension of the above crude solid (90 g, 0.41 mol) in 1/1 EtOH/EtOAc (600 μL) was added an additional 200 mL of warm EtOH to aid with solubilizing the compound. To this solution was added 5% Pd—C (9 g, wet, Degussa type) and the mixture placed under hydrogen (45 psi) on a Parr shaker. Hydrogen was recharged at 10 minutes and 30 minutes. The reaction was shaken for 1 h and then filtered through celite. The filter was rinsed with EtOH (2×200 mL) and concentrated to an oil which solidified on standing. To a solution of the solidified oil (155 g, 0.81 mol) in absolute EtOH (1.55 L) at 0° C. was added HCl (70 mL, 12N) dropwise, while the internal temperature was maintained below 5° C. The solution was stirred at 0° C. for 4 h and filtered. The filter cake was washed with cold EtOH (2×125 mL). The solids were collected and dried under vacuum for 15 h to give compound 1A (162 g, 87% yield) as a white crystalline solid. $^1$H NMR (DMSO-D$_6$, 400 MHz) δ 9.5 (br s, 2H), 8.27 (s, 1H), 7.53 (s, 1H), 7.40 (d, J=7.6 Hz, 1H), 7.11 (m, 1H), 2.60 (m, 1H), 2.13 (s, 3H), 0.45 (m, 2H), 0.34 (m, 2H); LCMS 191.1 (M+H); HPLC rt 0.58 min, YMC S5 ODS-A 4.6×50 mm, 4 min grad, 10% MeOH/H$_2$O to 90% MeOH/H$_2$O (0.2% H$_3$PO$_4$).

Step 1B.

To a suspension of 3-amino-N-cyclopropyl-4-methylbenzamide hydrochloride (1A) (22.7 g, 0.1 mol) in acetone (200 mL) was added 4-methyl morpholine (42.4 mL, 0.3 mol). The solution was cooled to −20° C. and chloroacetyl chloride (12 mL, 0.15 mol) was added dropwise. The reaction mixture was stirred at −10° C. for 10 min before being quenched with H$_2$O (200 mL). The precipitate formed was collected by vacuum filtration and dried to provide 25.3 g (95% yield) of 3-(2-chloro-acetylamino)-N-cyclopropyl-4-methylbenzamide, mp: 150° C. (dec.); $^1$H NMR (500 MHz, DMSO-D$_6$) δ 9.83 (s, 1H), 8.39 (d, J=3.8 Hz, 1H), 7.82 (s, 1H), 7.58 (d, J=6.6 Hz, 1H), 7.28 (d, J=8.3, 1H), 4.32 (s, 2H), 2.82 (m, 1H), 2.22 (s, 3H), 0.66 (m, 2H), 0.56 (m, 2H); $^{13}$C NMR (100 MHz, DMSO-D$_6$) δ: 167.2, 165.4, 136.0, 135.8, 132.8, 130.5, 124.8, 124.7, 43.4, 23.4, 18.1, 6.0; Anal. Calcd for C$_{13}$H$_{15}$ClN$_2$O$_2$: C, 58.54; H, 5.66; N, 10.50; Cl, 13.29. Found: C, 53.72; H, 5.95; N, 9.65; Cl, 13.52.

Example 2

3-(2-Chloroacetamido)-N-methyl-4-methylbenzamide

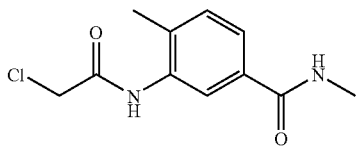

3-(2-Chloroacetamido)-N-methyl-4-methylbenzamide was prepared from 3-amino-N-methyl-4-methylbenzamide hydrochloride in 91% yield according to the method described for Example 1, Step 1B. mp: 200° C. (dec); $^1$H NMR (500 MHz, DMSO) δ: 2.22 (s, 3H), 2.75 (d, 3H, J=4.4), 4.31 (s, 2H), 7.29 (d, 1H, J=8.3), 7.58 (m, 1H), 7.84 (s, 1H), 8.37 (d, 1H, J=3.9), 9.79 (s, 1H); $^{13}$C NMR (500 MHz, DMSO) δ:17.54, 26.09, 42.96, 124.14, 130.13, 132.20, 134.80, 164.89, 165.88; m/z 241.28 (M+H); Anal. Calcd for C$_{11}$H$_{13}$ClN$_2$O$_2$: C, 54.89; H, 5.44; N, 11.64; Cl, 14.73. Found: C, 51.13; H, 5.39; N, 10.80; Cl, 16.61. 3-Amino-N-methyl-4-methylbenzamide hydrochloride was prepared using known methods as described, for example, in WO 03/091229 A1, to Dyckman et al.

Example 3

2-Bromo-5-(2-chloroacetamido)-N-methyl-4-methylbenzamide

Step 3A

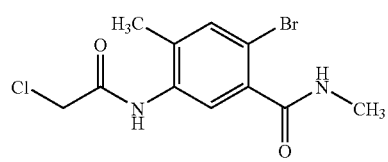

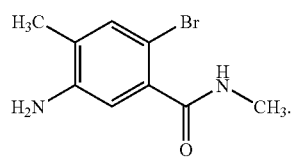

(3A)

To a solution of 2-methyl-5-methylcarboxamido-aniline (165 mg, 1 mmol) in DMF (5 mL) at 0° C. was added NBS (180 mg, 1 mmol). The solution was stirred for 10 minutes and slowly water (20 mL) was added. The product was extracted with EtOAc (3×30 mL), dried over Na$_2$SO$_4$, filtered and concentrated to an oil. The residue was purified on silica gel (50% EtOAc/heptane to 75% EtOAc/heptane and finally 100% EtOAc) to give 270 mg of compound 3A. $^1$H NMR: (CDCl$_3$, 400 MHz) δ 7.22 (s, 1H), 6.95 (s, 1H), 6.11 (br s, 1H), 3.00 (d, J=5.0 Hz, 3H), 2.14 (s, 3H); HPLC rt 1.05 min, 99.9% purity.

Step 3B.

To a solution of 5-amino-2-bromo-N, 4-dimethylbenzamide (3A) (94 mg, 0.38 mmol) in acetone (4 mL) at 0° C. was added DIPEA (68 μL, 0.39 mmol) followed by 2-chloroacetylchloride (31 μL, 0.39 mmol). The solution was stirred for 60 minutes and another aliquot of 2-chloroacetylchloride (4 μL) was added. Water was added (94 mL) and the acetone removed in vacuo. The solids were stirred rapidly for 1 h, filtered and washed with water to give 104 mg (84% yield) of 2-bromo-5-(2-chloroacetamido)-N-methyl-4-methylbenzamide, $^1$H NMR: (CDCl$_3$, 400 MHz) δ 8.28 (s, 1H), 8.03 (s, 1H), 7.44 (s, 1H), 6.01 (br s, 1H), 4.23 (s, 2H), 3.01 (d, J=5.0 Hz, 3H), 2.17 (s, 3H); LCMS 320.99 (M+H).

Compounds of Formula (III)

Examples 4 and 5 illustrate specific examples for making compounds of Formula (III).

Example 4

S-1-Sec-Butyl-3-dimethylaminomethylene-thiourea

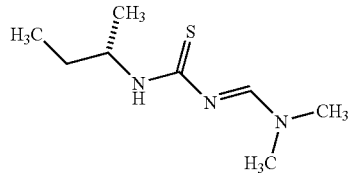

-continued

Step 4A. (S)-1-sec-Butylthiourea

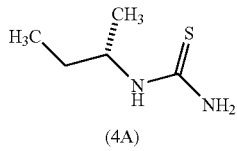

(4A)

To a solution of S-sec-butyl-amine (7.31 g, 0.1 mol) in chloroform (80 mL) at 0° C. was slowly added benzoyl isothiocyanate (13.44 mL, 0.1 mol). The mixture was allowed to warm to 10° C. and stirred for 10 min. The solvent was then removed under reduced pressure, and the residue was dissolved in MeOH (80 mL). An aqueous solution (10 mL) of NaOH (4 g, 0.1 mol) was added to this solution, and the mixture was stirred at 60° C. for another 2 h. The MeOH was then removed under reduced pressure, and the residue was stirred in water (50 mL). The precipitate was collected by vacuum filtration and dried to provide S-1-sec-butyl-thiourea (4A) (12.2 g, 92% yield). mp 133-134° C.; $^1$H NMR (500 MHz, DMSO-D$_6$) δ 7.40 (s, 1H), 7.20 (br s, 1H), 6.76 (s, 1H), 4.04 (s, 1H), 1.41 (m, 2H), 1.03 (d, J=6.1 Hz, 3H), 0.81 (d, J=7.7 Hz, 3H); $^{13}$C NMR (125 MHz, DMSO-D$_6$) δ 182.5, 50.8, 28.8, 19.9, 10.3; LRMS m/z 133.2 (M+H); Anal. Calcd for C$_5$H$_{12}$N$_2$S: C, 45.41; H, 9.14; N, 21.18; S, 24.25. Found: C, 45.49; H, 8.88; N, 21.32; S, 24.27.

Step 4B.

To a solution of 4A (13.2 g, 0.1 mol) in EtOH (200 mL) was added DMF-DMA (16 mL, 0.12 mol). The solution was heated at 73° C. for 20 min. The solvent was removed under reduced pressure and the residue was dissolved in EtOAc (200 mL). The insoluble impurity was discarded by vacuum filtration. The filtrate was concentrated under reduced pressure and the residue was crystallized in hexane to provide S-1-sec-butyl-3-dimethylaminomethylene-thiourea (Example 4) (18.3 g, 98% yield). mp 69-70° C.; $^1$H NMR (500 MHz, CDCl$_3$), ~3:2 mixture of isomers: major isomer δ 8.85 (s, 1H), 6.56 (br s, 1H), 4.48 (m, 1H), 3.10 (s, 3H), 3.00 (s, 3H), 1.49 (m, 2H); 1.19 (d, J=6.6 Hz, 3H), 0.92 (t, J=7.7 Hz, 3H); minor isomer δ 8.81 (s, 1H), 6.56 (br s, 1H), 4.22 (m, 1H), 3.13 (s, 3H), 3.06 (s, 3H), 1.60 (m, 2H); 1.12 (d, J=6.6 Hz, 3H), 0.87 (t, J=7.7 Hz, 3H); $^{13}$C NMR (100 MHz, CDCl$_3$) δ (191.9, 191.7), (164.0, 163.0), (52.1, 51.1), 41.7, (36.1, 35.9), (30.1, 29.6), (20.5, 19.9), (10.9, 10.8); LRMS m/z 188.33 (M+H); Anal. Calcd for C$_8$H$_{17}$N$_3$S: C, 51.29; H, 9.14; N, 22.43; S, 17.12. Found: C, 51.15; H, 9.21; N, 22.49; S, 17.14.

Example 5

(R)-1-sec-Butyl-3-((dimethylamino)methylene)thiourea

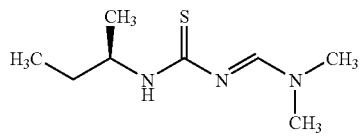

-continued

Step 5A (R)-1-sec-Butylthiourea

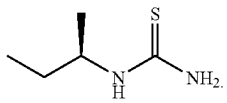

(R)-1-sec-Butylthiourea was prepared in 92% yield according to the method described for Example 4A. mp 133-134° C.; $^1$H NMR (500 MHz, DMSO) δ 0.80 (m, 3H, J=7.7), 1.02 (d, 3H, J=6.1), 1.41 (m, 2H), (3.40, 4.04)(s, 1H), 6.76 (s, 1H), 7.20 (s, br, 1H), 7.39 (d, 1H, J=7.2); $^{13}$C NMR (500 MHz, DMSO) δ: 10.00, 19.56, 28.50, 50.20, 182.00; m/z 133.23 (M+H); Anal. Calcd for C$_5$H$_{12}$N$_2$S: C, 45.41; H, 9.14; N, 21.18; S, 24.25. Found: C, 45.32; H, 9.15; N, 21.14; S, 24.38.

Step 5B. (R)-1-sec-Butyl-3-((dimethylamino)methylene)thiourea

Example 5 was prepared in 98% yield according to the method described for Example 4. mp 69-70° C.; $^1$H NMR (500 MHz, CDCl$_3$) δ 0.90 (m, 3H), 1.10 (d, 1H, J=6.6), 1.18 (d, 2H, J=6.6), 1.47 (m, 2H), 3.04 (q, 6H), (4.21, 4.46)(m, 1H), 6.58 (d, 1H, J=46.8), 8.80 (d, 1H, J=17.6); $^{13}$C NMR (500 MHz, CDCl$_3$) δ (10.27, 10.39), (19.41, 19.98), (29.11, 29.60), (35.45, 35.71), 41.25, (50.65, 51.64), (162.45, 163.52), (191.26, 192.41); m/z 188.33 (M+H); Anal. Calcd for C$_8$H$_{17}$N$_3$S: C, 51.29; H, 9.14; N, 22.43; S, 17.12. Found: C, 51.11; H, 9.40; N, 22.71; S, 17.43.

Compounds of Formula (I)

Examples 6 through 101 illustrate specific examples for making compounds of Formula (I).

Example 6

(S)-2-(sec-Butylamino)-N-(5-(cyclopropylcarbamoyl)-2-methylphenyl)thiazole-5-carboxamide

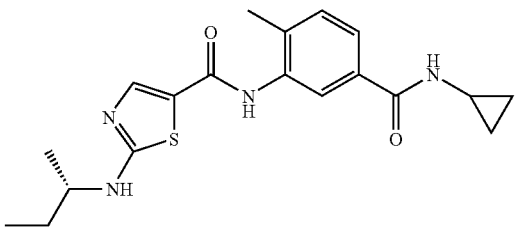

A solution of compound Example 1 (18.7 g, 0.1 mol) and Example 4 (26.7 g, 0.1 mol) in MeOH (100 mL) was stirred and refluxed for 6 h, then quenched with water. The precipitate was purified by crystallization from EtOH (active carbon), and the solid was stirred in water at 95° C. for 4 h. The final pure compound was collected by vacuum filtration and dried to provide Example 6. $^1$H NMR (500 MHz, DMSO) δ: 0.55 (m, 2H) 0.66 (td, J=7.01, 4.67 Hz, 2H) 0.87 (t, J=7.42 Hz, 3H) 1.14 (d, J=6.60 Hz, 3H) 1.51 (m, 2H) 2.22 (s, 3H) 2.83 (m, 1H) 3.62 (m, J=13.33, 6.87, 6.74 Hz, 1H) 7.30 (d, J=8.25 Hz, 1H) 7.60 (dd, J=8.25, 1.65 Hz, 1H) 7.73 (d, J=1.10 Hz, 1H) 7.89 (s, 1H) 8.10 (d, J=7.70 Hz, 1H) 8.37 (d, J=3.85 Hz, 1H) 9.61 (s, 1H); $^{13}$C NMR (500 MHz, DMSO) δ: 5.65, 10.32, 17.88, 19.70, 23.02, 28.60, 51.96, 120.07, 124.47, 125.55, 130.06, 132.30, 136.06, 137.11, 143.06, 159.72, 166.82, 171.21; m/z 373.20 [M+H]; Anal. Calcd for $C_{19}H_{24}N_4O_2S \cdot H_2O$: C, 58.44; H, 6.71; N, 14.35; S, 8.210. Found: C, 58.44; H, 6.47; N, 14.37; S, 8.18.

Example 7

(R)-2-(sec-Butylamino)-N-(2-methyl-5-(methylcarbamoyl)phenyl)thiazole-5-carboxamide

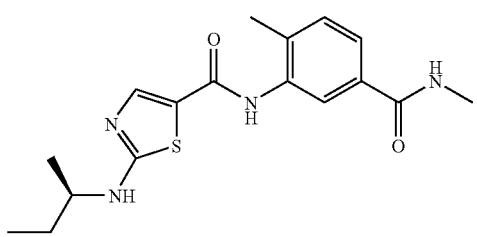

The above Example 7 was prepared from in 88% yield according to the method described for Example 6, using Examples 2 and 5 as starting materials. $^1$H NMR (500 MHz, DMSO) δ: 0.88 (t, 3H, J=7.2), 1.14 (d, 3H, J=6.6), 1.51 (m, 2H), 2.24 (s, 3H), 2.76 (d, 3H, J=4.4), 3.62 (m, 1H), 7.30 (d, 1H, J=7.6), 7.60 (dd, 1H, J=1.6, 6.0), 7.76 (s, 1H), 7.90 (s, 1H), 8.06 (d, 1H, J=7.6), 8.34 (d, 1H, J=4.4), 9.58 (s, 1H); $^{13}$C NMR (500 MHz, DMSO) δ: 10.30, 17.83, 19.67, 26.16, 28.59, 51.96, 120.05, 124.22, 125.42, 130.12, 132.41, 136.11, 136.88, 143.07, 159.71, 165.98, 171.21; m/z 345.3 [M−H]; Anal. Calcd for $C_{17}H_{22}N_4O_2S$: C, 58.93; H, 6.40; N, 16.17; S, 9.25. Found: C, 58.87; H, 6.49; N, 16.30; S, 9.14.

Example 8

(R)-N-(4-Bromo-2-methyl-5-(methylcarbamoyl)phenyl)-2-(sec-butylamino)thiazole-5-carboxamide

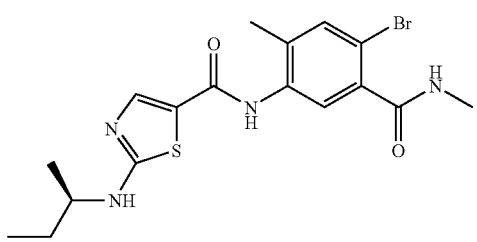

The above Example 8 was prepared in 83% yield according to the method described for Example 6, using Examples 3 and 5 as starting materials. $^1$H NMR: (DMSO-$D_6$, 400 MHz) δ 9.56 (s, 1H), 8.29 (m, 1H), 8.15 (d, J=7.9 Hz, 1H), 7.90 (s, 1H), 7.54 (s, 1H), 7.33 (s, 1H), 3.64 (m, 1H), 2.73 (d, J=4.6 Hz, 3H), 2.23 (s, 3H), 1.55) m, 1H), 1.15 (d, J=6.5 Hz, 3H), 0.89 (t, J=7.4 Hz, 3H); LCMS 427.1 (M+2H).

Example 9

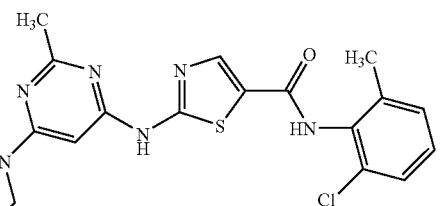

Step 9A

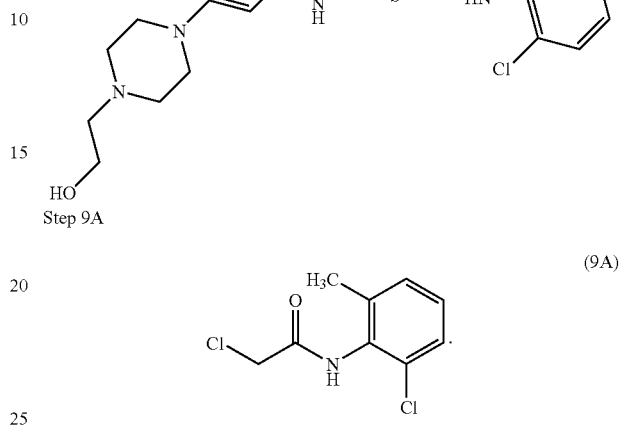

(9A)

The above compound 9A is prepared following the method described above for Example 1.

Step 9B

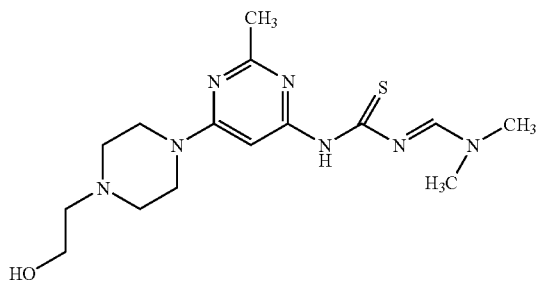

The above compound 9B is prepared following the method described above for Example 4.

Step 9C.

Example 9

The above compound of Example 9 is prepared following the method described for Example 6, using compounds 9A and 9B as starting materials.

Examples 10-101

Compounds having formulae (Ia), (Ib), (Ic), and (Id), wherein the variables have the values set forth in Tables 1, 2, 3 and 4, respectively, and wherein the compounds can be identified according to the characterization figures set forth in the tables, are prepared following the same methods described above in Examples 1 through 8, using the appropriate thiourea and arylamide compounds as starting materials.

TABLE 1
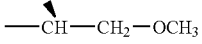
(Ia)
| Example No. | R⁴ | MS/HPLC |
|---|---|---|
| 10 |  | 389.1, 2.65 |
| 11 |  | 476.2, 3.50 |
| 12 | —(CH₂)₂OCH₃ | 375.2, 2.48 |
| 13 |  | 357.1, 2.64 |
| 14 |  | 371.1, 2.89 |
| 15 |  | 385.2, 3.00 |
| 16 |  | 399.1, 3.24 |
| 17 | 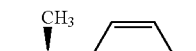 | 421.2, 3.31 |
| 18 |  | 425.1, 3.29 |
| 19 |  | 425.1, 3.32 |
| 20 |  | 425.1, 3.31 |
| 21 | 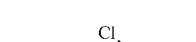 | 441.1, 3.49 |
| 22 |  | 441.1, 3.57 |
TABLE 1-continued
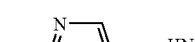
(Ia)
| Example No. | R⁴ | MS/HPLC |
|---|---|---|
| 23 |  | 441.1, 3.57 |
| 24 | 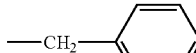 | 437.2, 3.27 |
| 25 |  | 437.2, 3.27 |
| 26 | 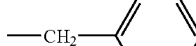 | 437.2, 3.22 |
| 27 |  | 408.0, 2.80 |
| 28 | 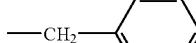 | 408.0, 2.08 |
| 29 |  | 408.0, 2.06 |
| 30 |  | 393.2, 3.44 |
| 31 | 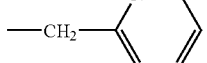 | 411.0, 3.61 |
| 32 |  | 411.2, 3.52 |

TABLE 1-continued (Ia) Structure: R⁴-NH-thiazole-C(O)-NH-(4-methylphenyl)-C(O)-NH-cyclopropyl

| Example No. | R⁴ | MS/HPLC |
|---|---|---|
| 33 | 2-chlorophenyl | 427.0, 3.52 |
| 34 | (3-fluoropyridin-2-yl)methyl (—CH₂-) | 426.1, 2.83 |
| 35 | 3-methylpyrrolidinyl | 386.1, 1.98 |
| 36 | —(CH₂)₂OH | 361.1, 2.23 |
| 37 | (4-fluoropyridin-3-yl)methyl (—CH₂-) | 426.1, 2.83 |
| 38 | H | 317.2, 1.83 |
| 39 | CH₃ | 331.1, 2.18 |
| 40 | —CH₂—CH₃ | 345.1, 2.42 |
| 41 | —(CH₂)₂CH₃ | 359.2, 2.72 |
| 42 | —CH—(CH₃)₂ | 359.2, 2.63 |
| 43 | —CH(CH₃)—CH₂—CH₃ | 373.3, 3.50 |
| 44 | —CH(CH₂CH₃)₂ | 387.2, 2.51 |
| 45 | —CH₂—CH(CH₃)₂ | 373.2, 2.98 |

TABLE 2

(Ib) Structure: R⁴-NH-(4-methylthiazole)-C(O)-NH-(4-methylphenyl)-C(O)-NH-cyclopropyl

| Example No. | R⁴ | MS/HPLC |
|---|---|---|
| 46 | —CH₂CH(CH₃)₂ | 387.2, 2.83 |
| 47 | —(CH₂)₂OCH₃ | 389.2, 2.39 |
| 48 | cyclopropyl | 371.2, 2.50 |
| 49 | cyclobutyl | 385.2, 2.74 |
| 50 | cyclopentyl | 399.2, 2.84 |
| 51 | cyclohexyl | 413.1, 3.08 |
| 52 | benzyl (—CH₂-phenyl) | 421.1, 3.13 |
| 53 | (S)-1-phenylethyl | 435.2, 3.22 |
| 54 | 2-fluorobenzyl | 439.2, 3.21 |
| 55 | 3-fluorobenzyl | 439.1, 3.28 |
| 56 | 4-fluorobenzyl | 439.1, 3.23 |
| 57 | 2-chlorobenzyl | 455.2, 3.46 |

TABLE 2-continued

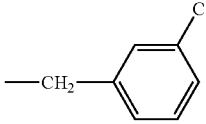

(Ib)

| Example No. | R⁴ | MS/HPLC |
|---|---|---|
| 58 | —CH₂—(3-chlorophenyl) | 455.1, 3.52 |
| 59 | —CH₂—(4-chlorophenyl) | 455.1, 3.51 |
| 60 | —CH₂—(2-methoxyphenyl) | 451.2, 3.14 |
| 61 | —CH₂—(3-methoxyphenyl) | 451.1, 3.18 |
| 62 | —CH₂—(4-methoxyphenyl) | 451.1, 3.12 |
| 63 | —CH₂—(2-pyridyl) | 422.1, 2.32 |
| 64 | —CH₂—(3-pyridyl) | 422.1, 2.17 |
| 65 | —CH₂—(4-pyridyl) | 422.0, 2.16 |
| 66 | —CH₂—(4-fluorophenyl, 3-methyl) | 425.1, 3.58 |
| 67 | —CH₂—CH₃ | 359.2, 2.34 |
| 68 | —(CH₂)₂CH₃ | 373.3, 2.56 |
| 69 | —CH—(CH₃)₂ | 373.2, 2.49 |
| 70 | —CH(CH₃)—CH₂—CH₃ | 387.2, 2.74 |

TABLE 3

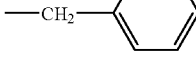

(Ic)

| Example No. | R⁴ | B | MS/HPLC |
|---|---|---|---|
| 70 | —CH—(CH₃)₂ | H | 319.1, 2.14 |
| 71 | —CH(CH₃)—CH₂—CH₃ | H | 333.1, 2.43 |
| 72 | —CH(CH₃)—CH₂—CH₃ | H | 333.1, 2.48 |
| 73 | cyclopentyl | H | 345.1, 2.61 |
| 74 | —(CH₂)₂CH₃ | —CH₂—CH₃ | 347.2, 2.63 |
| 75 | —CH—(CH₃)₂ | —CH₂—CH₃ | 347.2, 2.53 |
| 76 | —CH(CH₃)—CH₂—CH₃ | —CH₂—CH₃ | 361.2, 2.78 |
| 77 | —CH(CH₃)—CH₂—CH₃ | —CH₂—CH₃ | 361.2, 2.78 |
| 78 | —(CH₂)₂OCH₃ | —CH₂—CH₃ | 363.1, 2.36 |
| 79 | cyclopentyl | —CH₂—CH₃ | 373.2, 2.91 |
| 80 | —(CH₂)₂CH₃ | CH₃ | 333.1, 2.41 |
| 81 | —CH—(CH₃)₂ | CH₃ | 333.1, 2.39 |
| 82 | —CH(CH₃)—CH₂—CH₃ | CH₃ | 347.2, 2.58 |
| 83 | —(CH₂)₂OCH₃ | CH₃ | 349.1, 2.15 |
| 84 | cyclopentyl | CH₃ | 359.1, 2.69 |
| 85 | —CH—(CH₃)₂ | 5-methyl-1H-pyrazol-3-yl | 385.2, 2.57 |
| 86 | —CH—(CH₃)₂ | 1,5-dimethyl-1H-pyrazol-3-yl | 399.2, 2.17 |
| 87 | —CH—(CH₃)₂ | 3-methylisoxazol-5-yl | 386.1, 2.76 |
| 88 | H | CH₃ | 291.2, 1.69 |

TABLE 3-continued (Ic)

| Example No. | R⁴ | B | MS/HPLC |
|---|---|---|---|
| 89 | —CH—(CH₃)₂ | CH₃ | 347.1, 2.78 |
| 90 | —CH—(CH₃)₂ | —CH₂—CH₃ | 361.2, 3.00 |
| 91 | —(CH₂)₂CH₃ | H | 319.2, 2.40 |

TABLE 4

(Id)

| Ex. No. | R⁴ | Y | MS/HPLC |
|---|---|---|---|
| 92 | —CH(CH₃)—CH₂—CH₃ | —C(O)—N(CH₃)₂ | 361.2, 2.65 |
| 93 | —CH(CH₃)—CH₂—CH₃ | —C(O)—NH₂ | 333.1, 2.26 |
| 94 | —CH(CH₃)—CH₂—CH₃ | —C(O)—NH—CH₃ | 347.2, 2.42 |
| 95 | —CH(CH₃)—CH₂—CH₃ | —C(O)—NH—CH(CH₃)₂ | 375.3, 2.87 |
| 96 | —CH(CH₃)—CH₂—CH₃ | —C(O)—NH—CH₂CH₂CH₃ | 375.2, 2.93 |
| 97 | —CH(CH₃)—CH₂—CH₃ | —C(O)—NH—cyclopropyl | 373.3, 2.76 |

TABLE 4-continued (Id)

| Ex. No. | R⁴ | Y | MS/HPLC |
|---|---|---|---|
| 98 | —CH(CH₃)—CH₂—CH₃ | —C(O)—NH—CH₂CH₃ | 361.2, 2.63 |
| 99 | —CH(CH₃)—CH₂—CH₃ | —NH—C(O)—CH₃ | 347.2, 2.62 |
| 100 | —CH(CH₃)—CH₂—CH₃ | —NH—C(O)—CH₂CH₃ | 361.2, 2.88 |
| 101 | —CH(CH₃)—CH₂—CH₃ | —NH—C(O)—O—CH₂CH₃ | 377.3, 3.11 |

What we claim is:

1. A process for preparing a compound having the formula (I),

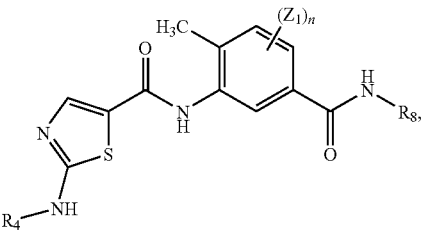

wherein $R_1$, $R_3$ and $R_5$ are H, $R_2$ is

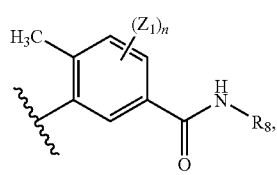

R$_4$ is alkyl or substituted alkyl, R$_8$ is alkyl or cyclopropyl, Z$_1$ is alkyl or halogen, and n is 0 or 1, comprising, (i) reacting a compound having the formula (II),

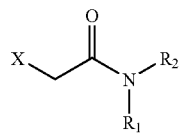
(II)

wherein X is a leaving group, and R$_1$ and R$_2$ are as defined above, (ii) with a compound having the formula (III)

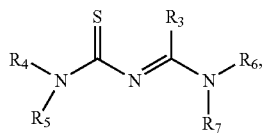
(III)

wherein R$_6$ and R$_7$ are (i) independently selected from alkyl, substituted alkyl, alkenyl, substituted alkenyl, alkynyl, substituted alkynyl, aryl, heteroaryl, cycloalkyl, and heterocyclo, or alternatively, (ii) R$_6$ and R$_7$ are taken together to form heteroaryl or heterocyclo;

(iii) to provide the compound having formula (I), above.

2. The process of claim 1, wherein X is R$_{11}$SO$_2$O—, and R$_{11}$ is selected from lower alkyl, trifluoromethyl, and tolyl.

3. The process of claim 1, wherein X is chlorine or bromine.

4. The process of claim 1, wherein the reaction of the compound of formula (II) with the compound of formula (III) is performed in the presence of a base.

5. The process of claim 1, wherein the reaction of the compound of formula (II) with the compound of formula (III) is performed in solvent without adding a base or catalyst.

6. The process of claim 1, wherein the reaction of the compound of formula (II) with the compound of formula (III), produces compounds of formula (I) in high yield.

7. The process of claim 1, wherein the compound of formula (III) is

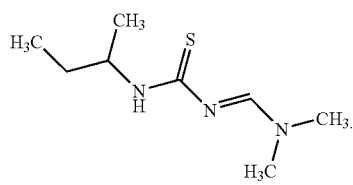

8. A process for preparing a compound having the formula (I),

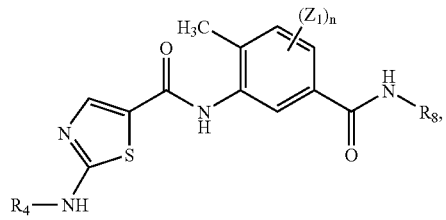

wherein R$_1$, R$_3$, R$_4$ and R$_5$ are as defined below, comprising, (i) reacting a compound having the formula (II),

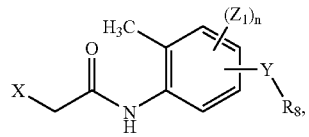

wherein R$_8$ is methyl, ethyl or cyclopropyl;
X is halogen; Z$_1$ is methyl or halogen; and n is 0, 1 or 2;

(ii) with a compound having the formula (III)

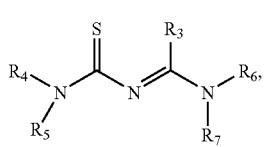
(III)

wherein R$_3$ and R$_5$ are H, R$_4$ is alkyl or substituted alkyl, and R$_6$ and R$_7$ are (i) independently selected from alkyl, substituted alkyl, alkenyl, substituted alkenyl, alkynyl, substituted alkynyl, aryl, heteroaryl, cycloalkyl, and heterocyclo, or alternatively, (ii) R$_6$ and R$_7$ are taken together to form heteroaryl or heterocyclo;

(iii) to provide the compound having formula (I), above.

9. The process of claim 1, wherein the compound of formula (II) is

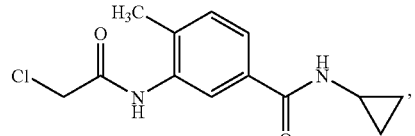

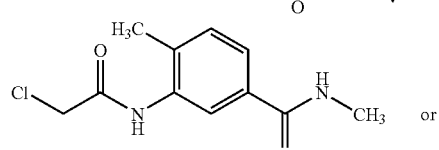 or

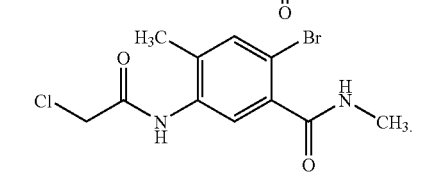

10. The process of claim 1, wherein the compound of formula (II) is prepared by
coupling of compounds of formula (2a),

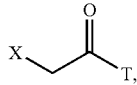

(2a)

wherein X is as defined in claim 1 and T is Cl, Br, or I, with amines having the formula (2b),

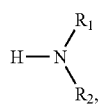

(2b)

wherein $R_1$ and $R_2$ are defined as in claim 1, to produce compounds of formula (II),

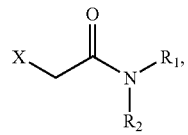

(II)

wherein when T is OH, the reaction is carried out in the presence of a coupling reagent.

11. The process of claim 1, wherein compound (III) is prepared by reacting a thiourea compound (3a)

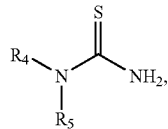

(3a)

wherein $R_4$ and $R_5$ are defined as in claim 1, with dialkoxy-N,N-disubstituted-alkylamine (3b),

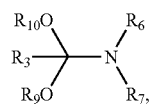

(3b)

wherein $R_3$, $R_6$ and $R_7$ are defined as in claim 1, and $R_9$ and $R_{10}$ are alkyl, to produce a compound having the formula (III).

12. The process of claim 1 or 8, wherein X is chlorine.

13. A process for preparing a compound having the formula (I),

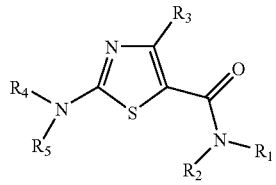

(I)

wherein $R_1$, $R_2$, $R_3$, $R_4$ and $R_5$ are as defined below, comprising,
(i) reacting a compound having the formula (II),

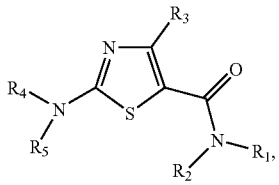

(I)

wherein X is $R_{11}SO_2O$—, $R_{11}$ is selected from lower alkyl, trifluoromethyl, and tolyl, and tolyl, and $R_1$ and $R_2$ are as defined below,
(ii) with a compound having the formula (III)

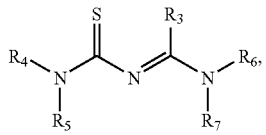

(III)

wherein $R_3$, $R_4$ and $R_5$ are as defined below and $R_6$ and $R_7$ are (i) independently selected from alkyl, substituted alkyl, alkenyl, substituted alkenyl, alkynyl, substituted alkynyl, aryl, heteroaryl, cycloalkyl, and heterocyclo, or alternatively, (ii) $R_6$ and $R_7$ are taken together to form heteroaryl or heterocyclo;
(iii) to provide the compound having formula (I), above, wherein,
$R_1$ is hydrogen;
$R_2$ is phenyl substituted with one to three of alkyl, halogen, —C(=O)NH—$R_8$, and/or —NHC(=O)—$R_8$, wherein $R_8$ is alkyl, cycloalkyl, or heteroaryl;
$R_3$ is the same in each of formulae (I) and (III), and is selected from hydrogen, cyano, haloalkyl, alkyl, substituted alkyl, alkenyl, substituted alkenyl, aryl, heteroaryl, cycloalkyl, and heterocyclo;
$R_4$ (i) is the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_4$ is taken together with $R_5$, to form heteroaryl or heterocyclo; and
$R_5$ (i) is the same in each of formulae (I) and (III), and (ii) is independently selected from hydrogen, alkyl, substituted alkyl, alkenyl, substituted alkenyl, alkynyl, substituted alkynyl, aryl, heteroaryl, cycloalkyl, and heterocyclo, or alternatively, $R_5$ is taken together with $R_4$, to form heteroaryl or heterocyclo.

* * * * *

UNITED STATES PATENT AND TRADEMARK OFFICE
CERTIFICATE OF CORRECTION

PATENT NO. : 7,652,146 B2
APPLICATION NO. : 11/049815
DATED : January 26, 2010
INVENTOR(S) : Bang-Chi Chen et al.

It is certified that error appears in the above-identified patent and that said Letters Patent is hereby corrected as shown below:

In the Claims:

Claim 5:

Column 35, line 48, after "in", insert -- a --.

Claim 8:

Column 36, lines 19 to 23, change

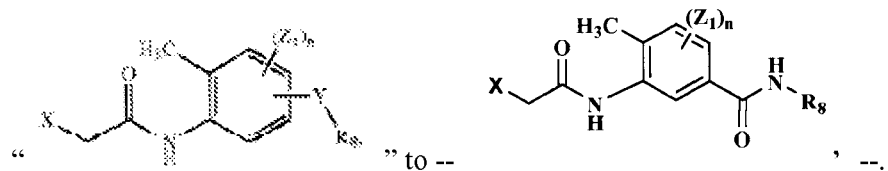

" to --

, --.

Claim 10:

Column 37, line 13, change "or I," to -- 1, or OH --.

Claim 13:

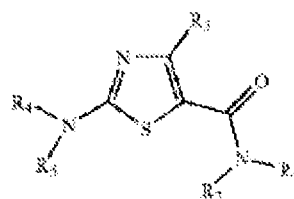

Column 38, lines 5 to 10, after "                ", insert -- , --.

Column 38, line 13, change "$R_1$" to -- $R_4$ --.

Signed and Sealed this
Eighth Day of November, 2011

David J. Kappos
*Director of the United States Patent and Trademark Office*

CERTIFICATE OF CORRECTION (continued)
U.S. Pat. No. 7,652,146 B2

In the Claims:

Claim 13 (continued):

Column 38, lines 17 to 23, change

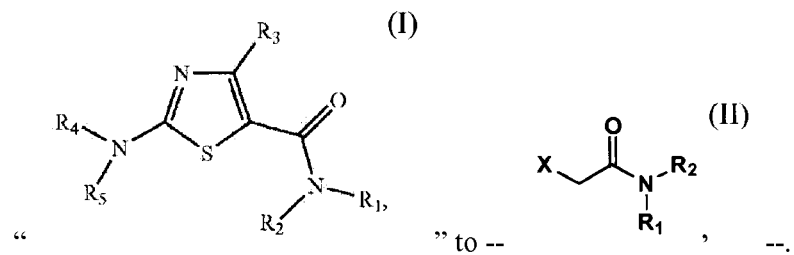

" to -- , --.

Column 38, line 27, after "trifluoromethyl,", delete "and tolyl,".